United States Patent
Tseng

[19]

[11] Patent Number: 5,997,300
[45] Date of Patent: Dec. 7, 1999

[54] FIXING DEVICE FOR A REMOVABLE ARTIFICIAL DENTURE

[76] Inventor: Hsien-Jung Tseng, 3F1 No. 142 Fraternity St., Hsin-Chu, Taiwan

[21] Appl. No.: 09/195,177

[22] Filed: Nov. 17, 1998

Related U.S. Application Data

[62] Division of application No. 09/061,009, Apr. 15, 1998, Pat. No. 5,871,357.

[51] Int. Cl.$^6$ .................................................. A61C 13/22
[52] U.S. Cl. ............................................................. 433/177
[58] Field of Search .................................. 433/172, 173, 433/177, 178

[56] References Cited

U.S. PATENT DOCUMENTS

| | | | |
|---|---|---|---|
| 3,328,879 | 7/1967 | Bax | 433/177 |
| 3,797,114 | 3/1974 | Wiland | 433/177 |
| 4,204,321 | 5/1980 | Scott | 433/177 |
| 4,214,366 | 7/1980 | Laban | 433/189 |
| 4,290,755 | 9/1981 | Scott | 433/173 |
| 4,547,156 | 10/1985 | Hader | 433/172 |
| 4,626,213 | 12/1986 | Shiner et al. | 433/173 |
| 4,787,851 | 11/1988 | Kusano et al. | 433/173 |
| 5,049,072 | 9/1991 | Lueschen | 433/173 |
| 5,417,570 | 5/1995 | Zuest et al. | 433/177 |
| 5,678,997 | 10/1997 | De Buck | 433/177 |
| 5,871,357 | 2/1999 | Tseng | 433/189 |

*Primary Examiner*—Ralph A. Lewis
*Attorney, Agent, or Firm*—Pro-Techtor International Services

[57] ABSTRACT

A fixing device for a removable denture mounted on the gingivals of an upper jaw or a lower jaw of a mouth. A stake is anchored in the base or root of the tooth, and a covering cup is mounted on the denture. An engaging member is placed in the cup chamber, the engaging member being a soft plastic annular member. When a ball head on the stake is engaged therein, the denture is fixed in place, the denture can also be drawn out for removal, so that mounting and removal of the denture at the area missing teeth is convenient.

1 Claim, 5 Drawing Sheets

FIXING DEVICE FOR A REMOVABLE ARTIFICIAL DENTURE

This is a divisional application of applicant's U.S. patent application Ser. No. 09/061,009, filed on Apr. 15, 1998 now U.S. Pat. No. 5,871,357.

BACKGROUND OF THE INVENTION

1. Field of the Invention

The present invention is related to a fixing device for a removable denture, and especially for such a device which is usable for a whole set, a partial denture, or a single artificial tooth on the gingiva of an upper jaw or a lower jaw of a mouth. With the present invention, the firmness of engagement of the denture of a patient after it is mounted can be effectively increased. Convenience for mounting as well as for removal of the denture is also provided.

2. Description of the Prior Art

Clinical cases relative to teeth loosening and falling out by virtue of periodontosis or other factors occur in proportion to age. In other words, older people have higher rates of losing teeth than young people. However, there are also cases of losing teeth in accidents unrelated to age. In some cases, only one or two of the teeth are missing. Dentists may deal with the patients missing teeth with a partial denture. The dentist may make a set of dentures coincident with the curvature of the gingiva of the remaining teeth or on a jaw, so that the patients can properly chew food and have their appearance restored.

The current art techniques of making dentures is to make a set of dentures (including the false teeth and the denture bases of the false teeth), and then adhere the upper and lower parts of the dentures between the upper and lower jaws and the gingivas by adherence of saliva in a wearer's mouth and by a vacuum condition caused when the denture bases of the false teeth and the mucous membranes of the gingivas are engaged. However, the adherence of the saliva and the vacuum condition is generally not adequate, according to the experience of many users. The upper denture is subjected to dropping when in biting food or opening his mouth wide. This mounting method is not applicable for those who only need mounting of a partial denture. Therefore, mounting of partial dentures or a single false tooth by the dentists is usually accomplished by a permanent installation, with the dentures being permanently secured and mounted at the positions missing teeth. Permanent mounting of the dentures leads to difficulty in cleansing the dentures.

SUMMARY OF THE INVENTION

The primary object of the present invention is to provide a fixing device for a removable denture that can be used for mounting a whole set or a partial denture. The device is convenient for mounting as well as for removing and cleansing the dentures.

To achieve the above stated object, when the fixing device of the present invention is mounted for use, the areas missing teeth on the upper and lower jaws in the mouth of a patient must have sound bases of teeth provided for mounting; this is because the present invention anchors stakes in a root or base of a tooth to achieve the effect of convenience for mounting as well as for removing a denture device. The device can be used to mount an entire set or a partial denture.

The present invention will be apparent in its practical structure and functions after reading the detailed description of the preferred embodiments thereof in reference to the accompanying drawings.

DETAILED DESCRIPTION OF THE PREFERRED EMBODIMENT

Figure 1:
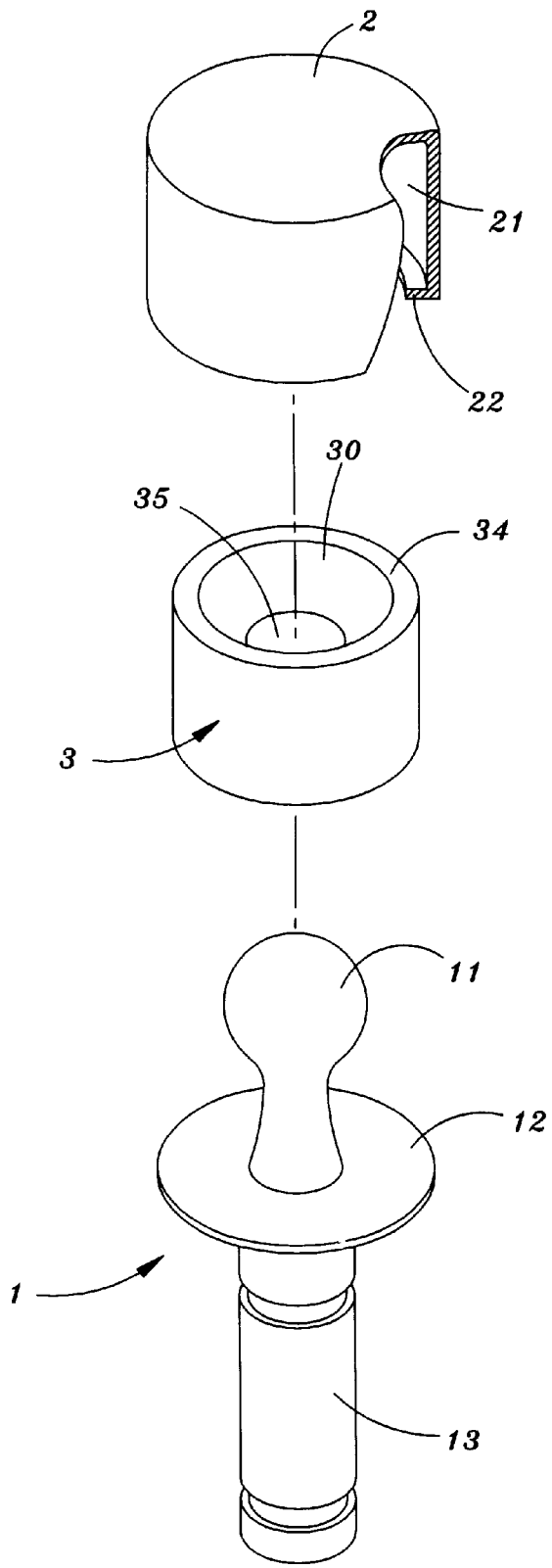
FIG. 1 is a perspective view of the fixing device for a removable denture of the present invention.

The fixing device for a removable denture provided in the present invention is made to have the shape as shown in FIG. 1, and is comprised of a stake 1, a covering cup 2 and an engaging member 3.

The stake 1 has a ball head 11, a disk-like shoulder 12 and a pin 13, all integrately formed.

The covering cup 2 has a cup chamber 21 and an inner annular rib 22 on the open end of the cup 2. The engaging member 3 is placed in the cup chamber 21.

Figure 3:
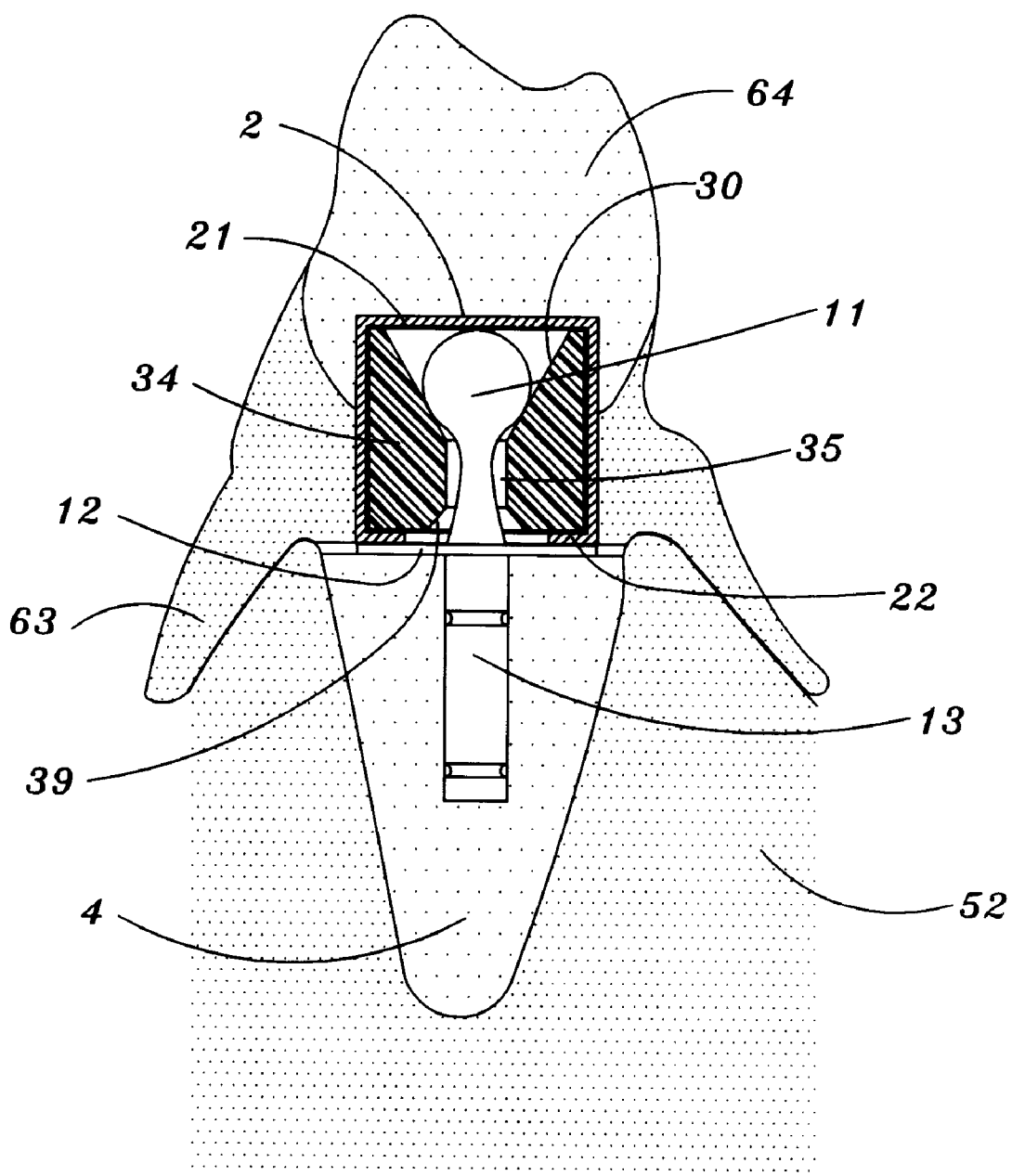
FIG. 3 is a schematic view showing assembling of the fixing device as depicted in FIG. 1.

The engaging member 3 is a soft plastic annular member 34 (such as shown in FIGS. 1 and 3). The annular member 34 is provided centrally with a shaped holding space 35 with a diameter smaller than that of the ball head 11. The annular member 34 is also mounted in the cup chamber 21 of the covering cup 2, and is prevented by the inner annular rib 22 from dropping. When in use, the ball head 11 on the stake 1 in the holding space 35 is tightly clamped by the soft plastic annular member 34. The annular member 34 is formed to have an upper conical surface 30 and a lower conical surface 39 as shown in FIG. 3. The upper conical surface 30 is provided to help firm holding of the ball head 11 of the stake 1. While the lower conical surface 39 is provided to help insertion of the ball head 11 into the holding space 35 and in the cup chamber 21 of the covering cup 2.

Figure 2:
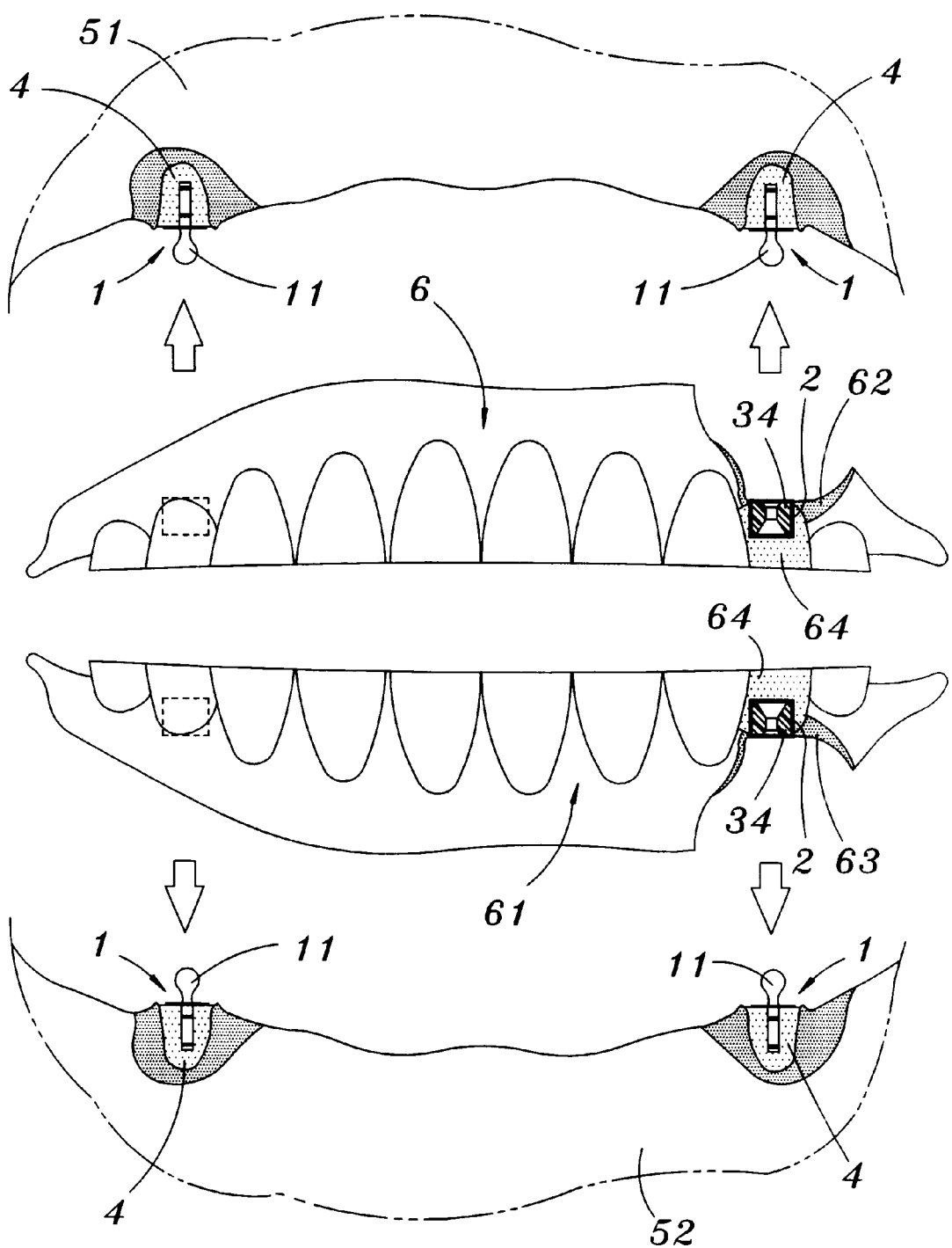
FIG. 2 is a schematic view of the present invention showing the fixing device used in mounting an upper and a lower denture.

When in use, a plurality of fixing devices of the present invention can be mounted on the dentures 6 and 61 for an upper jaw 51 and a lower jaw 52 (as shown in FIG. 2). The device can also be used for partial false teeth (only two or three teeth or a partial denture) on the upper jaw 51 and the lower jaw 52. The pins 13 on the stakes 1 are positioned in the base of the tooth 4 so that the disk-like shoulders 12 are exactly at the level of the gum line, and so that the stakes 1 are firmly secured.

The ball heads 11 of the stakes 1 are exposed to the areas above the disk-like shoulders 12 for supporting and engaging the false teeth. The covering cups 2 provided therein with the engaging members 3 are embedded in the joints between the bases 62, 63 of the dentures 6 and 61 and the bodies of the false teeth 64. The openings of the covering cups 2 are exposed and perform the engaging function for mounting the ball heads 11 of the stakes 1.

Figure 4:
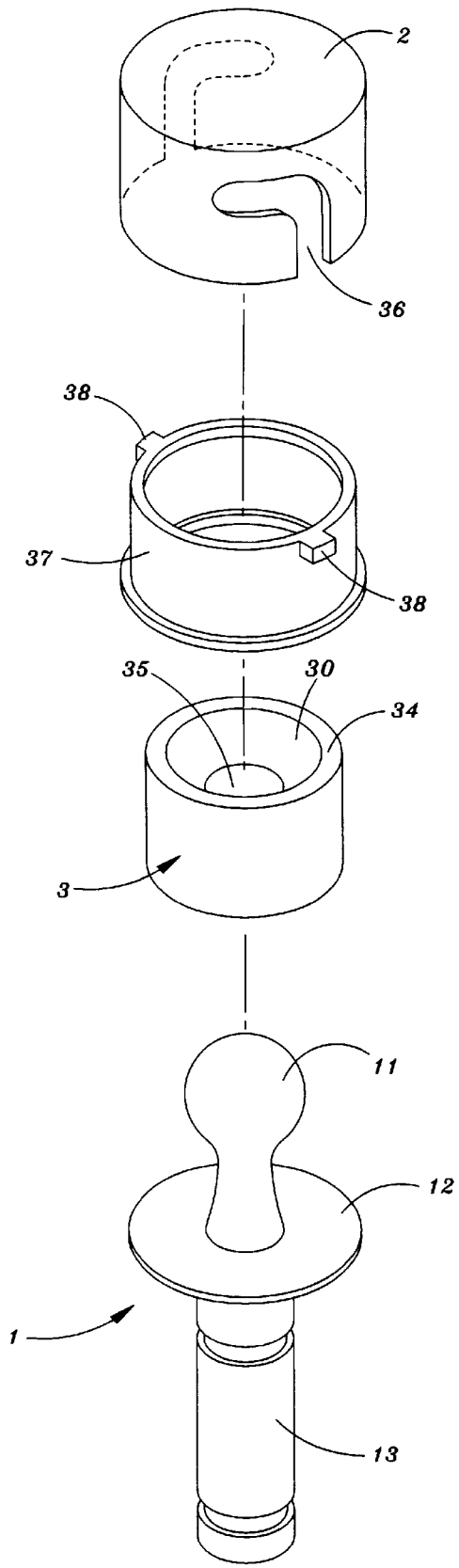
FIG. 4 is a perspective view of another embodiment of the fixing device for a removable denture of the present invention.
Figure 5:
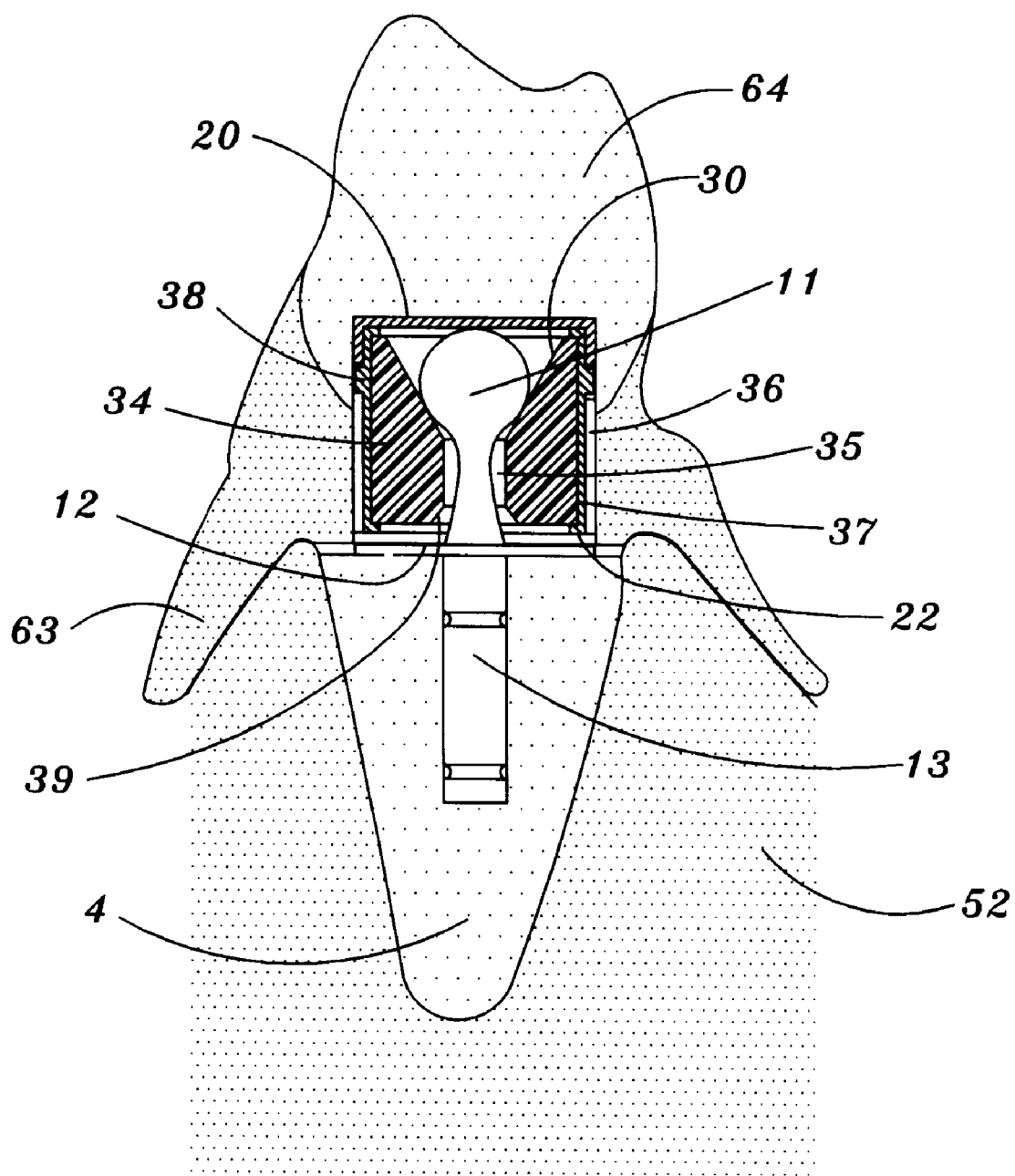
FIG. 5 is a schematic view showing assembling of the fixing device as depicted in FIG. 4.

When the annular member 34 is used in the engaging member 3, the wall of the covering cup 2 can be formed to have a pair of "L" shaped slots 36 as shown in FIGS. 4 and 5. The annular member 34 can be embedded in an annular collar 37 which is placed in the covering cup 20. The annular collar 37 is provided with a pair of lugs 38 which can be extended in the "L" shaped slots 36 so as to restrain the annular collar 37 with the annular member 34. This embodiment can not only effectively allow engagement and removal of the ball head 11 on the stake 1, but can also allow removal of the annular collar 37 from the covering cup 20 secured on the denture 61 to facilitate replacement of the annular member 34 which is subjected to wear in the annular collar 37.

Accordingly, the device of the present invention can be used to mount an entire set or partial denture on an upper jaw and a lower jaw of a mouth. The device provides effective as well as convenient mounting and removal of the denture. Convenience of removing for cleansing is also obtained.

The above disclosure is not intended as limiting. Those skilled in the art will readily observe that numerous modifications and alterations of the device may be made while retaining the teachings of the present invention. Accordingly, the above disclosure should be construed as limited only by the restrictions of the appended claims.

I claim:

1. A fixing device for a removable denture mounted on the gingivals of an upper jaw or a lower jaw of a mouth, said device is comprised of a stake, a covering cup and an engaging member, wherein:

said stake is adapted to be secured in the residual body of a tooth, a ball head of said stake is exposed to the area above the top of said residual body of said tooth;

said covering cup is fixedly mounted on said denture, and has a cup chamber and an inner annular rib on the opening end thereof, said engaging member is placed in said cup chamber;

said engaging member is a soft plastic annular member which is provided centrally thereof with a shaped holding space, said soft plastic annular member is mounted in said covering cup to engage and tightly clamp said ball head of said stake, so that said denture can be mounted and can be removed conveniently; and wherein said covering cup further includes on the wall thereof a pair of "L" shaped slots, an annular collar is additionally provided in said covering cup for engaging said soft plastic annular member, said annular collar is provided thereon with a pair of lugs extending respectively in said "L" shaped slots and can make turning therein to restrain said annular collar engaging said annular member so that, not only the capability of engagement and removal of said denture with and from said ball head of said stake is provided, but also removal of said annular collar for facilitating changing of said annular member which is subjected to wear in said annular collar is allowed, and life of use of said fixing device is increased.

* * * * *